United States Patent [19]
Tokieda et al.

[11] Patent Number: 5,168,326
[45] Date of Patent: Dec. 1, 1992

[54] METHOD OF DETECTING ANGLE OF OPTICAL ROTATION IN SOLUTION HAVING TIME-DEPENDENT CONCENTRATION, DETECTION APPARATUS THEREFOR, AND DETECTOR CELL THEREFOR

[75] Inventors: Tsunemi Tokieda; Norio Ishida, both of Tokyo, Japan

[73] Assignee: Showa Denko K.K., Tokyo, Japan

[21] Appl. No.: 735,557

[22] Filed: Jul. 25, 1991

[30] Foreign Application Priority Data

Jul. 27, 1990 [JP] Japan .................. 2-200234
Jul. 9, 1991 [JP] Japan .................. 3-168278

[51] Int. Cl.$^5$ .................. G01J 4/00; G01N 21/01
[52] U.S. Cl. .................. 356/368; 356/244; 356/246
[58] Field of Search .............. 356/364, 366, 367, 368, 356/365, 244, 246; 250/225

[56] References Cited

U.S. PATENT DOCUMENTS

| | | | |
|---|---|---|---|
| 3,738,755 | 6/1973 | Chaney et al. | 356/368 |
| 4,405,816 | 9/1983 | Skaletz | 204/59 R |
| 4,498,774 | 2/1985 | Yeung | 356/368 |
| 4,902,134 | 2/1990 | Spanier | 356/364 |
| 5,036,204 | 7/1991 | Leyden | 250/373 |

FOREIGN PATENT DOCUMENTS

| | | |
|---|---|---|
| 55-103434 | 8/1980 | Japan . |
| 61-83924 | 4/1986 | Japan . |
| 8803266 | 5/1988 | United Kingdom .............. 356/368 |

*Primary Examiner*—Richard A. Rosenberger
*Assistant Examiner*—Hoa Q. Pham
*Attorney, Agent, or Firm*—Sughrue, Mion, Zinn, Macpeak & Seas

[57] ABSTRACT

In a detection apparatus, a linearly polarized light beam polarized in a polarizer (62) is converted by being transmitted through a Pockels cell (60), driven by an alternative voltage, into an alternative linearly polarized light beam and a circularly polarized light beam, which is transmitted through a sample solution flowing through a flow cell (68). The transmitted light beam is separated into two polarized light components, and an intensity thereof is measured to obtain a signal proportional to an angle of rotation by the sample solution. A signal corresponding to an angle of rotation caused by an optical rotary power of the sample solution is obtained by subtracting the signal obtained during irradiation of the circularly polarized light from the signal obtained during irradiation of the linearly polarized light. The sample solution (18) is infused into an optical path of the flow cell (68) under a condition where mean velocity is 0.5 to 5 m/sec.

16 Claims, 8 Drawing Sheets

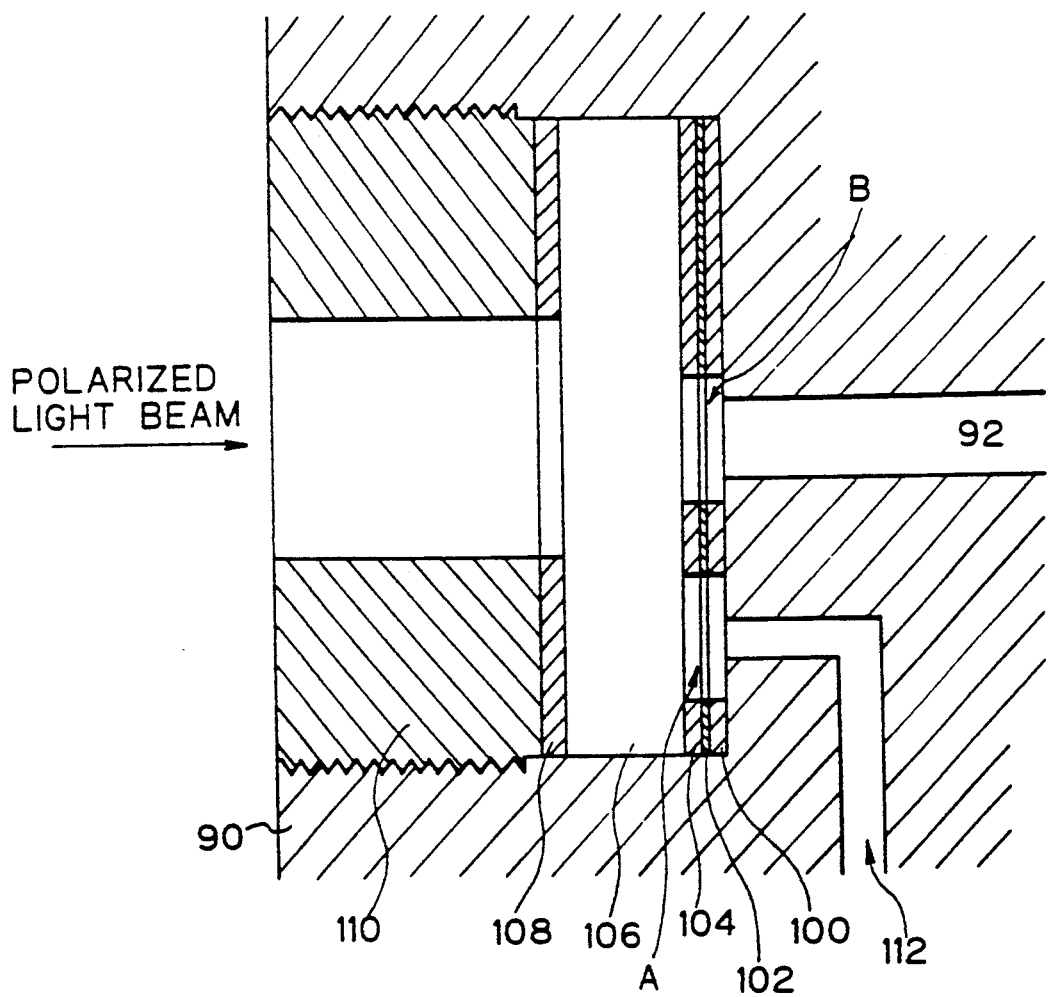

METHOD OF DETECTING ANGLE OF OPTICAL ROTATION IN SOLUTION HAVING TIME-DEPENDENT CONCENTRATION, DETECTION APPARATUS THEREFOR, AND DETECTOR CELL THEREFOR

BACKGROUND OF THE INVENTION

1. Field of the Invention

The present invention relates to a method of detecting an angle of optical rotation, and a detecting apparatus and a detector cell for realizing the method.

The measurement of the angle of rotation is utilized in a detector such as a detector of a liquid chromatograph, and realizes, for example, a qualification and determination of optically active substances by measuring an angle of rotation caused by the optically active substances contained in eluent discharged from a column of a liquid chromatograph.

2. Description of the Related Art

Recently, the creation of an optical resolution column has enabled analyses of optically active substances to be widely carried out by using a liquid chromatograph. Currently, some types of apparatuses for measuring the angle of rotation are also used as a means for detecting the optically active substances, in the liquid chromatograph.

One type of such apparatus comprises a Faraday cell for irradiating a sample solution with a linearly polarized light beam having a direction of vibration modulated by an alternative signal. The intensity of transmitted light is analyzed in an analyzer having a direction orthogonal to a mean direction of vibration of the irradiating polarized light and a photo-electric element. When the sample solution does not contain an optically active substance, the intensity gives an alternative current signal which does not contain a direct current component, and when the sample solution contains optically active substances, the intensity gives an alternative current signal which contains a direct current component corresponding to an angle of rotation by the sample solution. Accordingly, an output signal of the photo-electric element is synchronously demodulated with a modulation signal of the Faraday cell, to obtain a signal corresponding to the angle of rotation by the sample solution.

This type of detection apparatus is disclosed in Japanese Unexamined Patent Publication No. 55-103434, although the apparatus is not disclosed in the publication as a detection apparatus for liquid chromatograph but as an azimuthal polarimeter.

On the other hand, in a detection apparatus disclosed in Japanese Unexamined Patent Publication No. 61-83924, a sample solution is irradiated with a non-modulated linearly polarized light beam, and the intensity of transmitted light is analyzed in an analyzer having two directions orthogonal to each other and not parallel to that of the irradiating polarized light and two respective photo-electric elements. An angle of rotation by the sample solution is calculated from the two intensity values, using a certain formula.

However, since these detection apparatuses are based on a measurement principle of an azimuthal polarimeter wherein a sample solution filling a detector cell is stationary, where a detection is carried out while the sample solution flows through a flow cell at a constant flow velocity, a large noise signal due to a time-dependency of concentration of the sample appears in the output signal. If these azimuthal polarimeters are used as a detector of a liquid chromatograph, peaks in chromatogram are distorted and a large noise signal appears even while an optically non-active substance is passing through the detector cell, and therefore, it is difficult to use them as a detector of optical active substances in a liquid chromatograph, etc.

SUMMARY OF THE INVENTION

An object of the present invention is to provide a method of detecting an angle of rotation wherein a distortion of peaks or large noise signals on a base line do not appear even if the method is applied to a detection system, such as a liquid chromatograph, wherein the concentration of a sample flowing through a flow cell varies as time passes.

Another object of the present invention is to provide a detection apparatus for realizing the above method.

Still another object of the present invention is to provide a detector cell for realizing the above method.

In accordance with the present invention, there is provided a method of detecting an angle of optical rotation caused by an optical rotary power of substances contained in a flowing sample solution, comprising the steps of generating a first beam consisting of linearly polarized light and a second beam having an impartial polarization direction, transmitting the first beam and second beam through the sample solution flowing through a measurement passage of a flow cell, measuring a light intensity of at least one polarized light component of the transmitted light in at least one direction, obtaining a first signal corresponding to an angle of rotation of the sample solution against the first beam from the light intensity of the polarized light component of the transmitted light of the first beam, obtaining a second signal corresponding to an angle of rotation of the sample solution against the second beam from the light intensity of the polarized light component of the transmitted light of the second beam, and subtracting the second signal from the first signal to obtain a signal corresponding to the angle of optical rotation caused by an optical rotary power of substances contained in the sample solution.

In accordance with the present invention, there is also provided a method of detecting an angle of optical rotation caused by an optical rotary power of substances contained in a flowing sample solution, comprising the steps of generating at least one beam including a linearly polarized light beam, transmitting the beam through the sample solution flowing through a measurement passage of a flow cell, measuring a light intensity of at least one polarized light component of the transmitted light in at least one direction, and obtaining a signal corresponding to the angle of rotation of the sample solution from the light intensity of the polarized light component, and further comprising the step of infusing the sample solution into the measurement passage under a condition wherein mean velocity is 0.5 to 5 m/sec.

In accordance with the present invention there is also provided an apparatus for detecting an angle of optical rotation caused by an optical rotary power of substances contained in a flowing sample solution comprising means for generating a first beam consisting of linearly polarized light and a second beam having an impartial polarization direction, a flow cell having a measurement passage in which the sample solution transmitting the first beam and the second beam flows, means for measuring a light intensity of at least one polarized light component of the transmitted light in at least one direction, and calculating means for calculating a value corresponding to the angle of rotation of the sample solution from the light intensity of the transmitted light, and for subtracting the value obtained during an irradiation of the second beam from the value obtained during an irradiation of the first beam to obtain the angle of optical rotation caused by an optical rotary power of substances contained in the sample solution.

In accordance with the present invention, there is also provided an apparatus for detecting an angle of optical rotation caused by an optical rotary power of substances contained in a flowing sample solution comprising means for generating at least one beam including a linearly polarized light beam, a flow cell having a measurement passage in which the sample solution transmitting the beam flows, means for measuring a light intensity of at least one polarized light component of the transmitted light in at least one direction, and calculating means for calculating the angle of rotation of the sample solution from the light intensity of the polarized light component, wherein the flow cell also has an infusion passage for infusing the sample solution into the measurement passage under a condition where mean velocity is 0.5 to 5 m/sec.

In accordance with the present invention, there is also provided a detector cell for use in detecting an angle of optical rotation caused by optical rotary power of substances contained in a flowing sample solution, comprising a measurement passage formed so that the sample solution transmitting a light beam for detecting the angle of rotation flows in the passage, and an infusion passage formed so as to infuse the sample solution into the measurement passage and having a cross section of 0.005 to 0.02 mm$^2$.

BRIEF DESCRIPTION OF THE DRAWINGS

FIG. 7 is an enlarged cross-sectional view of the detector cell shown in FIG. 5;

DESCRIPTION OF THE PREFERRED EMBODIMENTS

Before describing the preferred embodiments according to the invention, examples of aforementioned related art are given with reference to the accompanying drawings.

Figure 1:
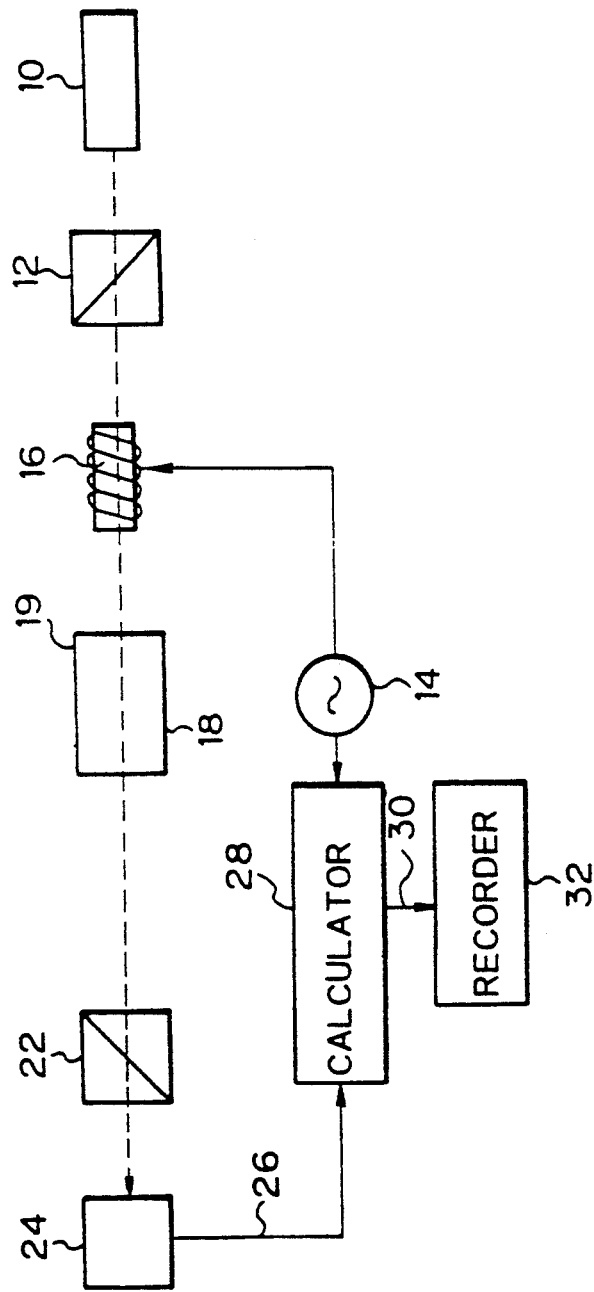
FIG. 1 is a block diagram of a first conventional detection apparatus for detecting an angle of rotation.

FIG. 1 is a block diagram of a first conventional detection apparatus measuring an angle of rotation using a Faraday cell. A light beam generated in a light source 10 having a certain wave-length purity is changed to a linearly polarized light beam having a modulated direction of vibration by an alternative signal, by a polarizer 12 and a Faraday cell 16 connected to an oscillator 14 generating an alternative current, and is transmitted through a sample solution 18 filling a cell 19. A light beam transmitted inside the cell 19 is rotated in a direction of vibration thereof by an optical rotary power of the sample solution 18 filling the cell 19, passes through an analyzer 22 arranged so that the analyzing direction thereof is orthogonal to the mean direction of vibration of the irradiating light beam, and is received by a light receiving element 24. When the sample solution filling the cell does not have an optical rotary power, a signal 26 output from the light receiving element 24 exhibit the same light intensity at the moment the direction of vibration is modulated to the right angle as that at the moment the direction of vibration is modulated to the left angle. On the other hand, when the sample solution contains some substances having an optical rotary power, those light intensities are not equal to each other, and a difference therebetween varies in proportion to the angle of rotation. Accordingly, by synchronously demodulating the signal 26 in a calculator 28 operating synchronously with the modulation, a continuous signal 30 which is proportional to the angle of rotation of the sample solution is obtained. The continuous signal 30 is recorded by a recorder 32.

Figure 2:
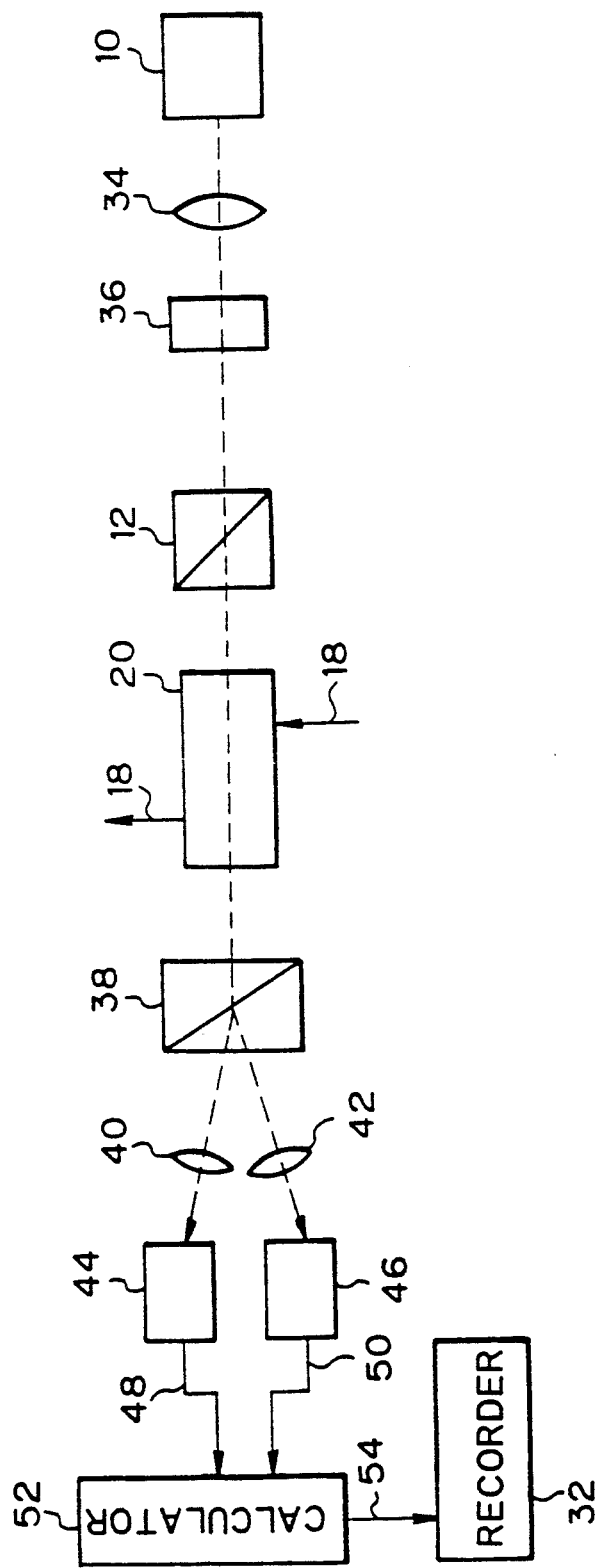
FIG. 2 is a block diagram of a second conventional detection apparatus for detecting an angle of rotation.

FIG. 2 is a block diagram of a detection apparatus disclosed in Japanese Unexamined Patent Publication No. 61-83924. As shown in FIG. 2, a light beam generated in a light source 10 passes through a lens 34 and a monochromatic filter 36, is changed to a linearly polarized light beam by a polarizer 12, and is transmitted inside a flow-cell 20. A light beam transmitted through the flow-cell 20 is separated into two light beams by an analyzer 38 arranged so that two light beams having directions of vibration orthogonal to each other and having the same light intensities as each other are formed when the sample solution 18 filling the flow cell 20 does not have an optical rotary power. The separated two beams pass through respective lenses 40 and 42 and are received by respective light receiving elements 44 and 46. The ratio of two output signals 48 and 50 from the respective light receiving elements 44 and 46 has a certain relationship to the angle of rotation in the sample solution 18 filling the flow cell 20. Therefore, by executing an operation on the two signals according to a relational expression, a continuous signal 54 which is proportional to the angle of rotation in the sample solution is obtained.

If the aforementioned type of detection apparatus for detecting the angle of rotation is used as, for example, a detector of a liquid chromatograph, a concentration of a sample flowing through the flow cell varies as time passes. Therefore, a spatial distribution of solutes in a passage of the flow cell is generally not uniform, and gradients of a refractive index must be irregularly generated as far as the solutes have a different refractive index from that of a solvent, whether or not the solutes have an optical rotary power. Micro-portions of the gradients of refractive index can be thought of as boundary faces bounding spaces having different refractive indexes from each other. When these boundary faces are irradiated with a linearly polarized light beam at a certain angle of incidence, it is apparent from Fresnel's formulas of transmission and reflection that an intensity of transmitted light of a component having a polarization plane parallel to the incident plane is not equal to that of another component having a polarization plane orthogonal to the incident plane, among the linearly polarized light beam. A condition where a summation of the unequality does not affect a direction of vibration of the linearly polarized light beam could not be realized if any displacement of the inlet of the eluent or imperfection of a passage in the flow cell exists. This phenomenon is observed as an apparent optical rotation as a whole, and its magnitude varies as time passes.

It can be concluded that noise signals on a baseline of a chromatogram and a distortion of peaks are generated by these mechanisms, whether or not a sample flowing through the flow cell has an optical rotary power.

The preferred embodiments of the present invention will now be described with reference to the accompanying drawings.

Figure 3:
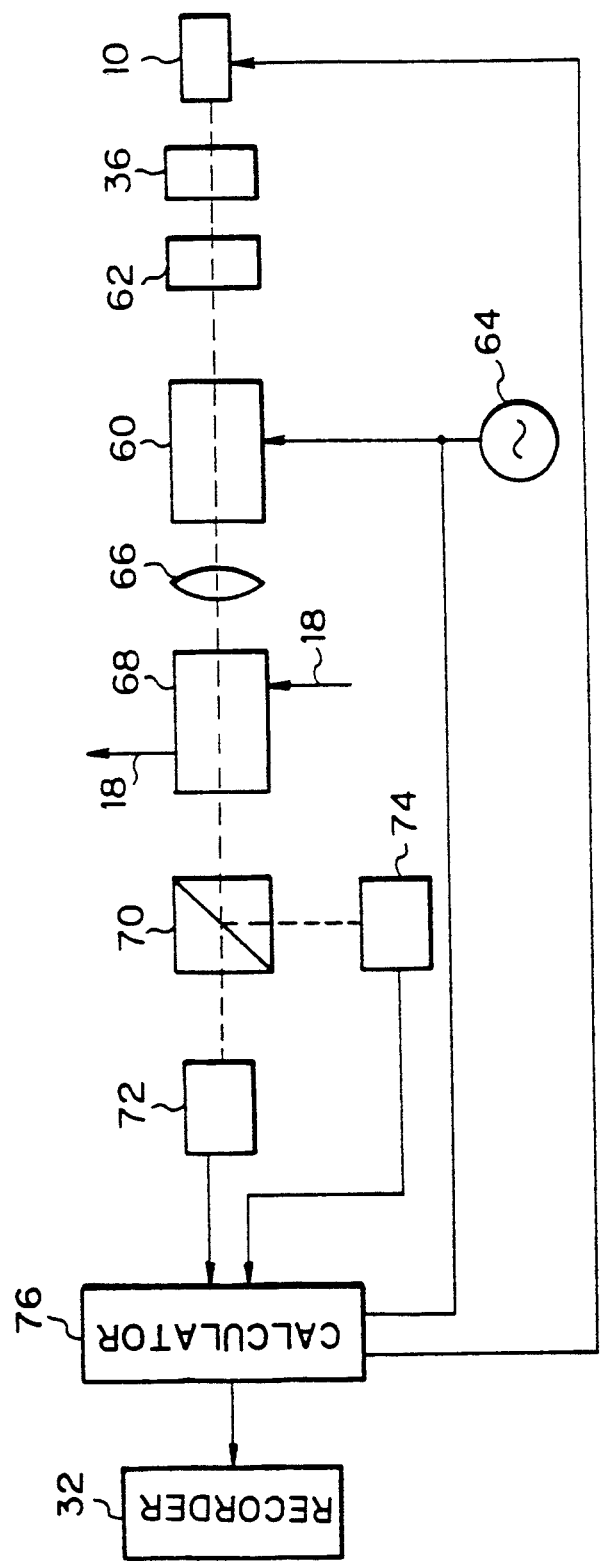
FIG. 3 is a block diagram of a detection apparatus according to a first embodiment of the present invention.

FIG. 3 is a block diagram of an apparatus for detecting an angle of rotation according to a first embodiment of the present invention. In FIG. 3, a light source 10 comprises a light emitting diode having a much narrower range of variation of intensity of the emitted light than that of a laser and a mercury lamp, having a very narrow radiation spectrum whose central wave-length is 730 to 790 nm, and having a maximum emission intensity of 10 to 30 mW, and a microlens having an outer diameter of 4 mm for makinq rays of light from the light emitting diode parallel. A monochromic filter 36 improves a purity of wave-length of the light beam from the light source 10, to obtain a more accurate circularly polarized light in a Pockels cell 60. A polarizer 62 is a sheetlike dichroic polarizing plate having an about $10^{-4}$ combined extinction ratio and is provided with a rotation adjustment mechanism to accurately adjust an angle of rotation. A Pockels cell 60 driven by an oscillator 64 is relatively compact and is made of a monocrystal of $LiNbO_3$ which operates at a low voltage. When a predetermined voltage is applied, the Pockels cell 60 changes incident linearly polarized light to circularly polarized light by phase-shifting one polarized light component at an angle of 45° from a direction of vibration of the incident linearly polarized light in relation to another polarized light component orthogonal to the former by 90°, and when the voltage is not applied, the Pockels cell 60 transmits the linearly polarized light. Thus, the Pockels cell 60 alternatively provides a linearly polarized light beam and a circularly polarized light beam in response to the alternative signal from the oscillator 64. Also, the Pockels cell 60 is provided with a rotation adjustment mechanism to accurately adjust an angle of rotation. A lens 66 efficiently introduces the light beam into a flow cell 68 through which a sample solution having time-dependent concentration flows. The flow cell 68 has an inner diameter of 0.5 to 1.5 mm and an optical path length of 10 to 50 mm, has an inlet and an outlet at both ends of the optical path, and is made of stainless steel. An analyzer 70 is a dielectric multilayer type cubic polarization beam splitter having an extinction ratio of 0.02, design wave-length of 780 nm, and size of 10×10×10 mm. The analyzer 70 is arranged at an angle of 45° from the direction of vibration of the polarizer 62. Light receiving elements 72 and 74 are silicon photo-diodes which covert light intensities of two light beams separated by the analyzer 70 into electrical signals. A calculator 76 inputs electrical signals from the two light receiving elements 72 and 74, in synchronization with the oscillator 64, and separately and successively calculates a difference between two signals from the light receiving elements 72 and 74 while the flow cell 68 is irradiates with the linearly polarized light, and a difference between two signals from the light receiving elements 72 and 74 while the flow cell 68 is irradiated with the circularly polarized light. Furthermore, the calculator 76 subtracts the difference obtained during the irradiation of the circularly polarized light from the difference obtained during the irradiation of the linearly polarized light, and outputs the difference signal as a chromatogram signal. The chromatogram signal is recorded by a recorder 32.

The following is a description of the influence imposed on a light beam transmitted by sample solution having a gradient of a refractive index, for the period when a linearly polarized light beam enters the flow cell, and the period when a circularly polarized light beam enters the flow cell, in the present invention.

First, the period when the linearly polarized light beam enters the flow cell is considered. In the linearly polarized light beam transmitted by the sample solution, a direction of the polarization is rotated in response to an optical rotary power of the sample solution, according to the following equation.

$$\delta = \alpha \cdot C \cdot L \qquad (1)$$

In the equation (1), $\delta$ is a rotation angle of the polarization direction caused by the optical rotary power of the solution, $\alpha$ is a specific rotary power of substance contained in the solution, C is a concentration of the substance, and L is an optical path length of the flow cell.

When an apparent angle of rotation caused by a gradient of a refractive index according to time-dependent variation of concentration of the sample solution is represented by $\epsilon$, a total angle of rotation $\delta_p$ of a polarization direction including an apparent rotation of a transmitted light beam is represented as the following equation (2).

$$\delta_p = \alpha \cdot C \cdot L + \epsilon \qquad (2)$$

Next, the period when a beam having an impartial polarization direction and a light intensity equal to that of the linearly polarized light beam, for example, a circularly polarized light beam, enters the flow cell is considered. Since a polarization direction of the circularly polarized light beam is not fixed and is uniformly distributed in all directions, an intensity of a polarized light component of the transmitted light beam in any direction does not vary, and thus a rotation of a polarization direction caused by an optical rotary power of the sample is not detected.

On the other hand, if a linearly polarized light beam is decomposed into two polarized light components orthogonal to each other and at an angle of 45° from a polarization direction of the linearly polarized light, two polarized light components having an equal intensity and phase are obtained. If a circularly polarized light beam is also decomposed into two polarized light components in the same directions as before, two polarized light components having an equal intensity but shifted in phase by 90° from each other are obtained. Assuming that the intensity of the linearly polarized light beam is equal to the intensity of the circularly polarized light, the intensity of the polarized light components of the linearly polarized light beam is equal to that of the circularly polarized light beam. In this case, since an apparent magnitude of an effect created by the gradient of a refractive index according to time-dependent variation of concentration of a sample in the flow cell is independent of a phase of the light, a magnitude of variation in the intensity of the polarized light components of the linearly polarized light caused by the gradient of a refractive index must be equal to that of the circularly polarized light.

Therefore, an apparent rotation angle $\delta_c$ of the polarization direction of the light beam transmitted by the sample solution, during the period in which the beam having impartial polarization direction enters the flow cell, is represented by the following equation (3).

$$\delta_c = \epsilon \quad (3)$$

Accordingly, a rotation angle $\delta_s$ obtained by subtracting the apparent rotation angle $\delta_c$ of the polarization direction obtained during an irradiation of the light beam having a impartial polarization direction from the apparent rotation angle $\delta_p$ of the polarization direction obtained during an irradiation of the linearly polarized light beam is that shown by the following equation (4).

$$\delta_s = \delta_p - \delta_c = (\delta + \epsilon) - \epsilon = \delta \quad (4)$$

The right side of the equation (4) depends only on the optical rotary power, and thus the equation shows that the effect of the gradient of the refractive index has been removed.

The removal of the effect of the gradient of the refractive index has been described, but regarding removal of the gradient itself, it was experimentally confirmed that the gradient of the refractive index can be remarkably improved by introducing the sample solution into the measurement passage under a condition wherein mean velocity is 0.5 to 5 m/sec.

In this condition, in a normal liquid chromatograph measurement, the inflow velocity of the sample solution becomes about a hundred times as large as a mean linear velocity in the optical path, and therefore a strong agitation near the inlet is obtained and the gradient of the refractive index is remarkably improved.

When a cross section of the infusion passage is 0.01 mm², the mean velocity is about 2 m/sec under a normal liquid chromatograph condition, and this condition is optimum. If the mean velocity is less than 0.5 m/sec, i.e., a cross section of the infusion passage is too large, a sufficient improvement is not obtained, and if the mean velocity is more than 5 m/sec, i.e., a cross section of the infusion passage is too small, other obstructions such as an elevation of the tube pressure arise.

In addition, the calculator 76 also has a function of controlling the light intensity of the light source 10 so that a sum of the intensity of the incident light on the two light receiving elements 72 and 74 is a constant value. The oscillator 64 outputs a rectangular wave or a sine wave having a frequency of 0.1 to 10 kHz and a maximum voltage of 1000 to 1500 V.

A tungsten lamp may be used for the light source 10, and a Glan-Taylor polarizing prism or a Glan-Thomson polarizing prism utilizing double refraction may be used as the polarizer 62. The material of the Pockels cell is not limited to the LiNbO₃, and any material which can shift a phase of one of the polarized light components in relation to another polarized light component, orthogonal to the former by 90° in response to an electric field or magnetic field, for example, a liquid crystal having a ferroelectricity, may be used as the material of the Pockels cell. Also, a Wollaston prism or a Rochon prism may be used as the analyzer 70.

The detection apparatus described with reference to FIG. 3 is created by simplifying the conventional detection apparatus described with reference to FIG. 2, and by introducing the concept of the present invention, Namely, in the conventional apparatus of FIG. 2, the intensity ratio of the two polarized light components separated by the analyzer 38 is calculated and the angle of rotation is calculated from the ratio using a specific formula, but in the apparatus of FIG. 3, a signal proportional to the angle of rotation by the sample solution is an intensity difference between the two polarized light components. Under a condition of a usual chromatograph measurement the angle of rotation $\delta$ is extremely small, and therefore, it can be assumed that the difference between the two is approximately proportional to the angle of rotation.

Figure 4:
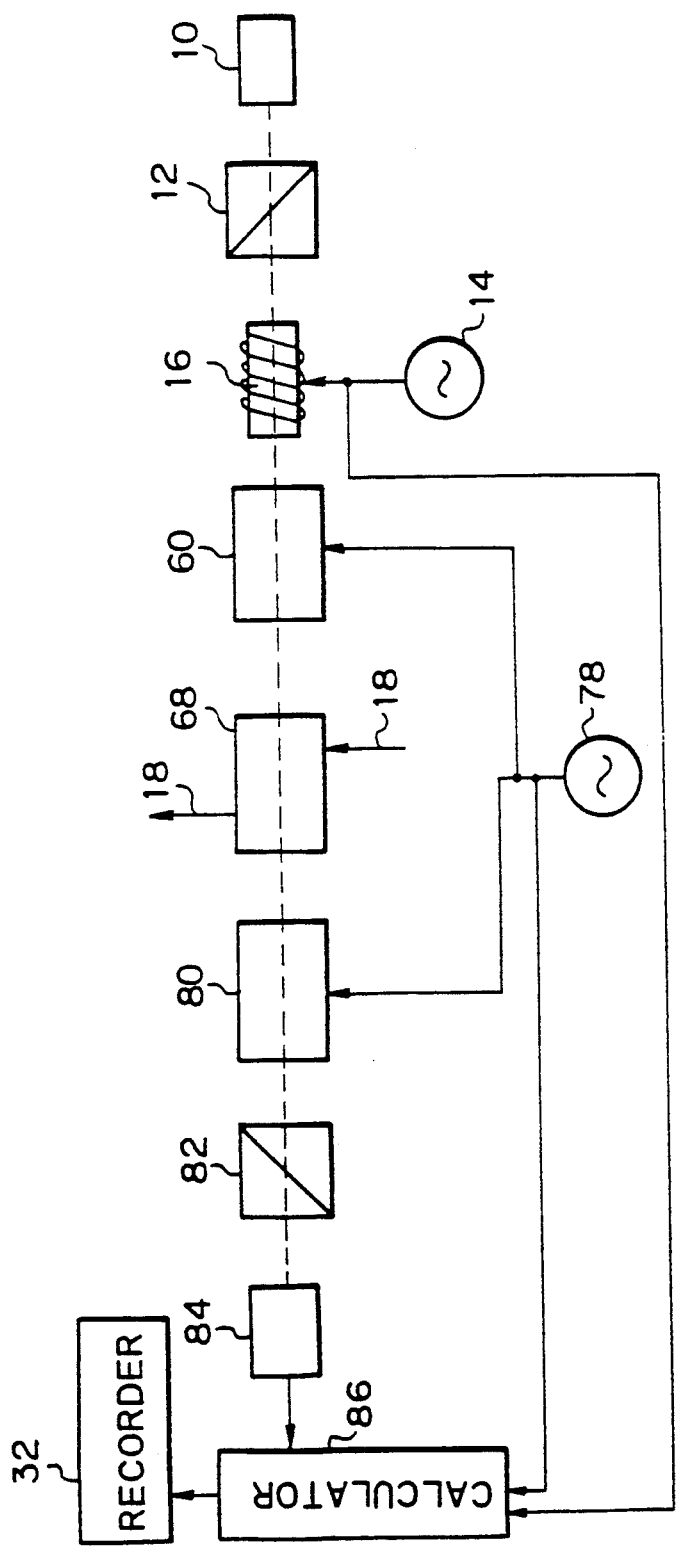
FIG. 4 is a block diagram of a detection apparatus according to a second embodiment of the present invention.

Introducing the concept of the present invention into the apparatus described with reference to FIG. 1 is also possible, and a detection apparatus according to a second embodiment of the present invention shown in FIG. 4 corresponds to this concept. In FIG. 4, a light beam having a certain wave length purity, from a light source 10, is polarized in a polarizer 12 to form a linearly polarized light beam. A direction of vibration of the linearly polarized light beam is modulated in a Faraday cell 16 connected to an oscillator 14 generating an alternative current. The light beam having the modulated direction of vibration enters a Pockels cell 60 driven by an alternative signal from the oscillator 78, and a linearly polarized light and a circularly polarized light are alternatively transmitted. A sample solution 18 flowing through a flow cell 68, and having a time-dependent concentration, transmits the linearly or circularly polarized light beam which is converted to a linearly polarized light beam by a Pockels cell 80 synchronously driven with the Pockels cell 60 by the oscillator 78. The light beam transmitted by the Pockels cell 80 enters an analyzer 82 arranged so that the direction of vibration thereof is orthogonal to that of the polarizer 12, and the light beam transmitted by the analyzer 82 is received by a light receiving element 84. A calculator 86 operating synchronously with the oscillator 78 and the oscillator 14 calculates a first signal wherein a signal proportional to an angle of rotation caused by an optical rotary power of the sample solution 18 is superimposed on a signal proportional to an angle of rotation caused by a gradient of refraction index, due to a time-dependent variation of a concentration of the sample solution 18, from an input signal obtained during an irradiation of the linearly polarized light beam, and a second signal proportional to an angle of rotation caused by the gradient of a refraction index from an input signal obtained during an irradiation of the circularly polarized light beam, and subtracts the second signal from the first signal to output a chromatogram signal. The chromatogram signal is recorded by the recorder 32.

Figure 5:
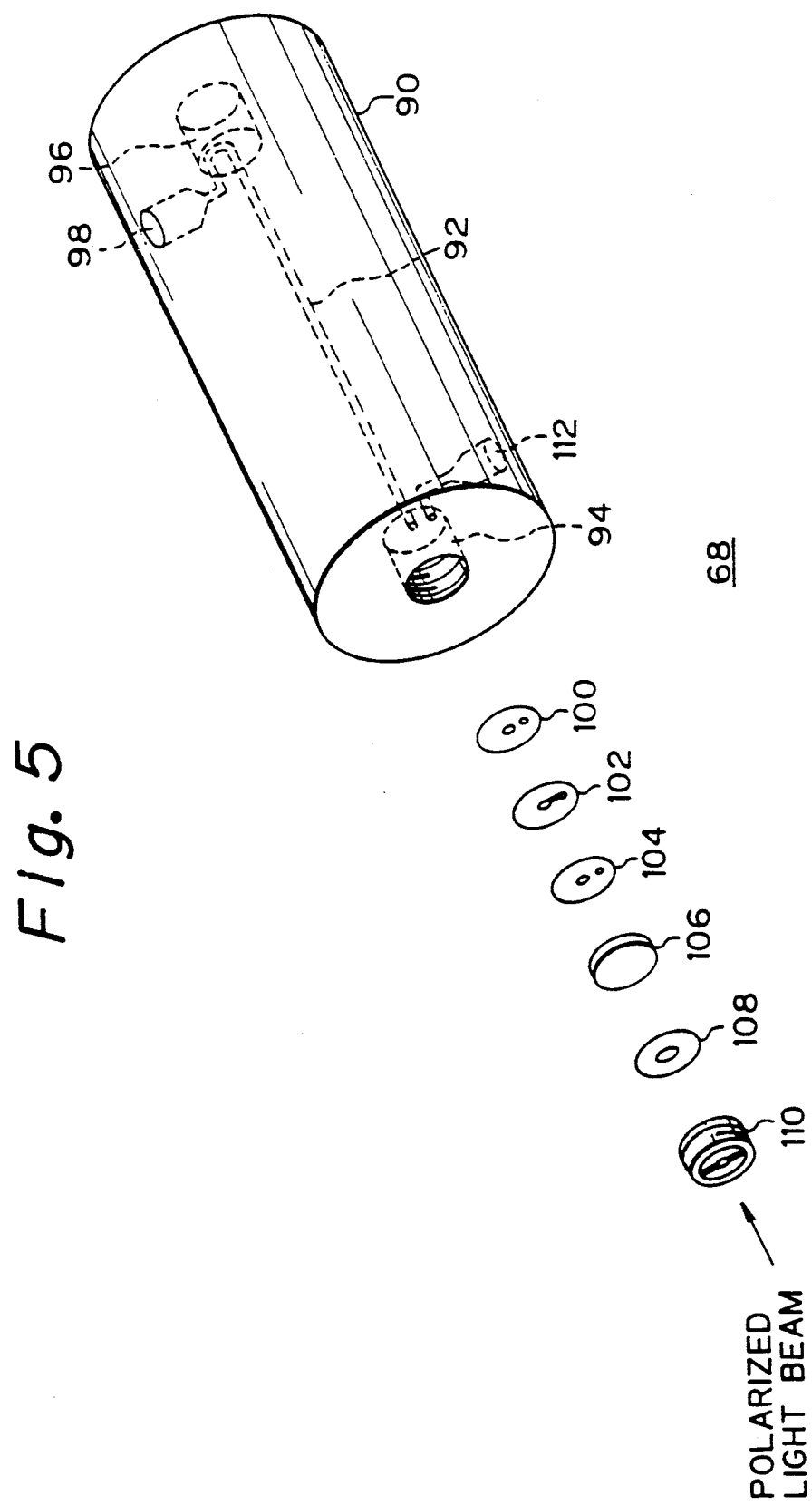
FIG. 5 is a separated perspective view of a detector cell according to an embodiment of the present invention.

FIG. 5 is a separated perspective view of a flow cell for measuring an angle of rotation according to an embodiment of the present invention.

A body 90 of the flow cell 68 is cylindrical and has a coaxially cylindrical passage for measurement 92. Coaxially cylindrical hollows 94 and 96 are formed at inlet and outlet sides of the measurement passage 92. Although not shown in detail, a spacer is fitted in the hollow 96 at the outlet side. The spacer is shaped so as to form a passage for connecting the measurement passage 92 to an outlet 98. Spacers 100, 102 and 104 having a circular external form are fitted in the hollow 94 of inlet side, and in addition, a cell window 106 and a packing 108 are fitted in the hollow 94, and the whole is made compact by pressure from a screwed-down slit holder 110.

Figure 6A:
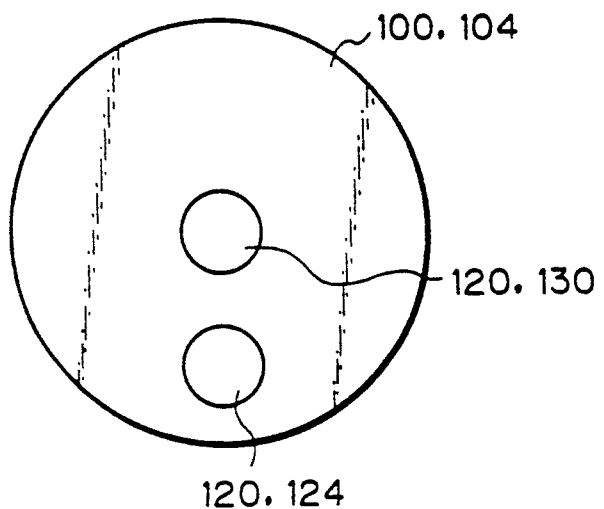
FIGS. 6A and 6B are plan views of spacers 100, 102 and 104 shown in FIG. 5.
Figure 6B:
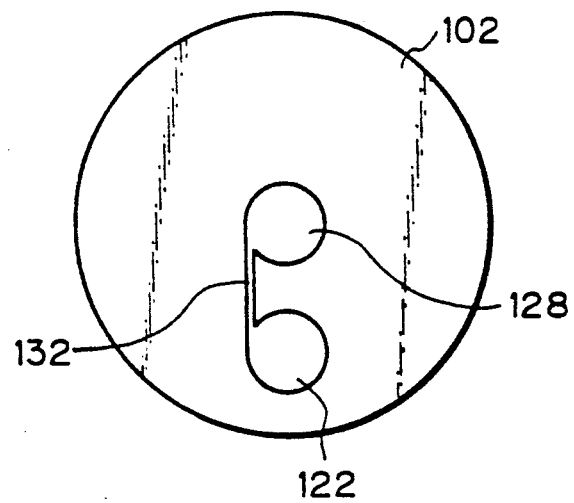

FIGS. 6A and 6B are plan views of the spacer 100 and 104 fitted in the hollow 94 and the spacer 102 interposed therebetween, as shown in FIG. 5, and FIG. 7 is an enlarged cross-sectional view of a portion near the inlet 112 of the flow cell 68 shown in FIG. 5.

A space A (FIG. 7) formed by three circular apertures 120, 124 and 122 (FIGS. 6A and 6B) made at corresponding positions off-set from the center of the spacer 100, 104 and a part of a surface of the cell window 106, and a space B (FIG. 7) formed by three circular apertures 126, 130 and 128 (FIG. 6A and 6B) made at the center of each spacer and a part of a surface of the cell window 106 are connected through a passage formed by a slit 132 made in the spacer 102 and parts of the surfaces of the spacer 100 and 104. Accordingly, a sample solution fed from the inlet 112 flows through this passage into the measurement passage 92.

If the thickness of spacer 102 is 0.1 mm and the slit 132 has a width of 0.1 mm, a cross section of the passage becomes 0.01 mm$^2$.

When the cross section of the passage is 0.01 mm$^2$, the mean velocity becomes about 2 m/sec under a normal measurement condition of a liquid chromatograph, and in this condition, an optimum improvement of a distortion of the peaks was obtained. When the cross section of the passage is more than 0.02 mm$^2$, i.e., when the mean velocity is less than 0.5 m/sec, this remarkable improvement was not obtained, and when the cross section of the passage is less than 0.005 mm$^2$, i.e., when the mean velocity is more than 5 m/sec, other obstructions such as a too high tube pressure arose.

Figure 8A:
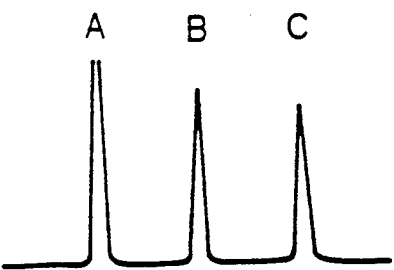
FIG. 8A is a chromatogram obtained by using a differential refractometer.
Figure 8B:
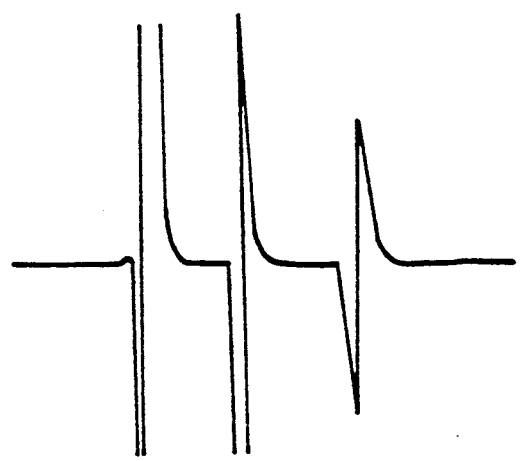
FIG. 8B is a chromatogram obtained by using a conventional apparatus for detecting an angle of rotation.
Figures 8C, 8D:
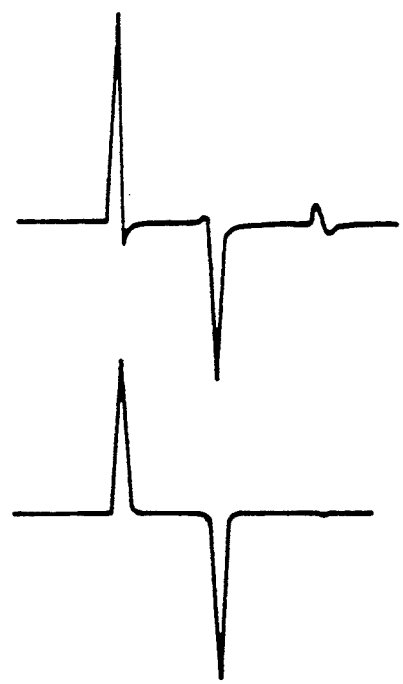
FIG. 8C is a chromatogram obtained by using a conventional apparatus using a detector cell according to the present invention.
FIG. 8D is a chromatogram obtained by using a detection apparatus according to the present invention, using a detector cell according to the present invention.

Chromatograms of a solution containing sucrose, fructose and ethanol were measured by using a detecting apparatus according to the present invention, a differential refractometer, or a conventional detecting apparatus for detecting an angle of rotation, as a detector of a chromatograph. FIGS. 8A to 8D are chromatograms obtained by these measurement. In these figures, letter A denotes peaks of sucrose, which has a positive optical rotary power, letter B denotes peaks of fructose, which has a negative optical rotary power, and letter C denotes peaks of ethanol, which does not have an optical rotary power. FIG. 8A shows a chromatogram obtained by a detector of the differential refractometer. FIG. 8B shows a chromatogram obtained by a detector using a conventional flow cell and the conventional detection apparatus. FIG. 8C shows a chromatogram obtained by a detector using a flow cell according to the present invention and the conventional detection apparatus. FIG. 8D shows a chromatogram obtained by a detector using the flow cell according to the present invention and the detection apparatus according to the present invention, wherein linearly polarized light and circularly polarized light are used. As shown in FIG. 8C, the distortion of peaks and appearance of noise are remarkably improved by using the flow all according to the present invention, and as shown in FIG. 8D, a noise signal due to ethanol substantially does not appear by additionally employing the detection apparatus wherein a linearly polarized light beam and a circularly polarized light beam are alternatively transmitted.

We claim:

1. A method of detecting an angle of optical rotation caused by an optical rotary power of substance contained in a flowing sample solution, comprising the steps of:
    i) generating a first beam consisting of linearly polarized light and a second beam having an impartial polarization direction,
    ii) transmitting the first beam and second beam through the sample solution flowing through a measurement passage of a flow cell,
    iii) measuring the light intensity of at least one polarized light component of the transmitted light in at least one direction,
    iv) obtaining a first signal corresponding to an angle of rotation of the sample solution against the first beam from the light intensity of the polarized light component of the transmitted light of the first beam,
    v) obtaining a second signal corresponding to an angle of rotation of the sample solution against the second beam from the light intensity of the polarized light component of the transmitted light of the second beam, and
    vi) subtracting the second signal from the first signal to obtain a signal corresponding to the angle of optical rotation caused by an optical rotary power of substance contained in the sample solution.

2. A method as claimed in claim 1, wherein the second beam having an impartial polarization direction is a circularly polarized light beam.

3. A method as claimed in claim 2, wherein the first beam of linearly polarized light and the second beam of circularly polarized light are alternatively generated by transmitting a beam of linearly polarized light through an optical element to which an alternating electric field is applied in the step i), wherein the optical element shifts the phase of a first polarized light component of transmitted light in relation to a second polarized light component orthogonal to the first polarized light component by 90°, while an electric field is applied to the optical element to thereby change the linearly polarized light to circularly polarized light.

4. A method as claimed in claim 3, wherein the optical element is a Pockels cell.

5. A method as claimed in claim 1, wherein the light intensities of the two polarized light components are measured respectively in two directions orthogonal to each other and at an angle of 45° from the polarization direction of the linearly polarized light, in step iii), and the first and second signals are obtained by subtracting the light intensity value in one direction from the light intensity value in another direction in steps iv) and v).

6. A method as claimed in claim 1, further comprising the step of infusing the sample solution into the measurement passage mean velocity of 0.5 to 5 m/sec.

7. A method of detecting an angle of optical rotation caused by an optical rotary power of substance contained in a flowing sample solution comprising the steps of:

ii) generating at least one beam including a linearly polarized light beam, iii) transmitting the beam through the sample solution flowing through a measurement passage of a flow cell, iv) measuring the light intensity of at least one polarized light component of the transmitted light in at least one direction, and v) obtaining a signal corresponding to the angle of rotation of the sample solution from the light intensity of the polarized light component, and further comprising the step of vi) infusing the sample solution into the measurement passage at a mean velocity of 0.5 to 5 m/sec.

8. An apparatus for detecting an angle of optical rotation caused by an optical rotary power of substance contained in a flowing sample solution comprising:

means for generating a first beam of linearly polarized light and a second beam having an impartial polarization direction;

a flow cell having a measurement passage through which the sample solution transmitting the first beam and the second beam can flow;

means for measuring a light intensity of at least one polarized light component of the transmitted light in at least one direction; and calculating means for calculating a value corresponding to the angle of rotation of the sample solution from the light intensity of the transmitted light, and for subtracting the value obtained during irradiation of the second beam from the value obtained during irradiation of the first beam to obtain the angle of optical rotation caused by an optical rotary power of substance contained in the sample solution.

9. An apparatus as claimed in claim 8, wherein the second beam having an impartial polarization direction is a circularly polarized light beam.

10. An apparatus as claimed in claim 9, wherein the generating means includes:

a linearly polarized light beam generator for generating a light beam of linearly polarized light, and an optical element connected to an oscillator generating an alternating voltage, for receiving the light beam and for alternatively outputting the first beam of linearly polarized light and the second beam of circularly polarized light, wherein the optical element shifts the phase of a first polarized light component of transmitted light in relation to a second polarized light component orthogonal to the first polarized light component by 90° while an electric field is applied to the optical element to thereby change the linearly polarized light to circularly polarized light.

11. An apparatus as claimed in claim 10, wherein the optical element is a Pockels cell.

12. An apparatus as claimed in claim 8, wherein the measuring means measure the light intensity of two polarized light components respectively in two directions orthogonal to each other and at an angle of 45° from a polarization direction of the linearly polarized light, and the calculating means calculates the value corresponding to the angle of rotation of the sample solution by subtracting the light intensity value in one direction from the light intensity value in another direction measured in the measuring means.

13. An apparatus as claimed in claim 8, wherein the flow cell also has an infusion passage for infusing the sample solution into the measurement passage at a mean velocity of 0.5 to 5 m/sec.

14. An apparatus as claimed in claim 8, wherein the flow cell further has an infusion passage, formed so as to infuse the sample solution into the measurement passage, and having a cross section of 0.005 to 0.02 mm$^2$.

15. An apparatus for detecting an angle of optical rotation caused by an optical rotary power of substance contained in a flowing sample solution comprising:

means for generating at least one beam including a linearly polarized light beam;

a flow cell having a measurement passage through which the sample solution transmitting the beam can flow;

means for measuring the light intensity of at least one polarized light component of the transmitted light in at least one direction; and calculating means for calculating the angle of rotation of the sample solution from the light intensity of the polarized light component, wherein the flow cell also has an infusion passage for infusing the sample solution into the measurement passage at a mean velocity of 0.5 to 5 m/sec.

16. An apparatus as claimed in claim 15, wherein the infusion passage has a cross section of 0.005 to 0.02 mm$^2$.

* * * * *